United States Patent [19]

Ohta et al.

[11] 4,024,180

[45] May 17, 1977

[54] PROCESS FOR THE PRODUCTION OF PERACETIC ACID

[75] Inventors: Nobuto Ohta, Tokyo; Juichi Imamura, Chofu; Takehiko Matsuzaki, Tokyo, all of Japan

[73] Assignee: Agency of Industrial Science & Technology, Tokyo, Japan

[22] Filed: May 8, 1968

[21] Appl. No.: 732,800

[30] Foreign Application Priority Data

Nov. 27, 1967 Japan ............................... 42-74679
Dec. 12, 1967 Japan ............................... 42-79258
Jan. 18, 1968 Japan ............................... 43-2366
Feb. 24, 1968 Japan ............................... 43-11373
Feb. 24, 1968 Japan ............................... 43-11374
Mar. 5, 1968 Japan ............................... 43-13809

[52] U.S. Cl. .......................................... 260/502 A
[51] Int. Cl.² ...................................... C07C 179/12
[58] Field of Search ............ 260/502, 502 A, 502 R

[56] References Cited

UNITED STATES PATENTS 3,228,977  1/1966  Sennewald et al. ............... 260/502
R25,057  10/1961  Stevens .......................... 260/502 A

*Primary Examiner*—James O. Thomas, Jr.
*Assistant Examiner*—W. B. Lone
*Attorney, Agent, or Firm*—Ernest G. Montague; Karl F. Ross; Herbert Dubno

[57] ABSTRACT

A process for the production of peracetic acid which comprises the steps of adding, to an inner solvent, acetaldehyde and at least one catalyst selected from the group consisting of strongly acidic carboxylic acids, strongly acidic phenols and nitric acid, and introducing oxygen gas or oxygencontaining gas into the resulting mixture while stirring the mixture and maintaining it at a temperature range of $-5°$ C to $50°$ C.

6 Claims, No Drawings

PROCESS FOR THE PRODUCTION OF PERACETIC ACID

This invention relates to a process for the production of peracetic acid. More particularly, this invention relates to a process for the production of peracetic acid characterized by, in an inert solvent, oxidizing acetaldehyde with oxygen or oxygen-containing gas by using, as a catalyst, (i) carboxylic acids, phenols or nitric acid which are soluble and strongly acidic in the reaction solution, (ii) the acidic substances mentioned in (i) (hereinafter referred to as "acidic catalyst") plus soluble salts of valence changeable heavy metal, (iii) acidic salts of the above acidic catalyst, said salts being soluble in a reaction solution and containing as a metal component a valence changeable heavy metal, or (iv) heavy metal salts of strongly acidic monocarboxylic acid, strongly acidic monophenol or nitric acid plus hydrogen chloride or its aqueous solution, said heavy metal being valence changeable.

Peracetic acid has a wide variety of utility in organic synthesis especially as an important oxidizing agent. Heretofore, it was well known that peracetic acid can be produced by a method which comprises oxidizing acetaldehyde at about 0° C to produce acetaldehyde monoperacetate (hereinafter referred to as "AMP") and decomposing the resulting AMP at about 100° C into peracetic acid and aldehyde. In this method, however, two steps are involved, and, in addition, highly explosive AMP is produced as an intermediate, so this method requires a high level of technique. It is also well known to produce peracetic acid by the gaseous phase oxidation of acetaldehyde, but, since the acetaldehyde and oxygen mixed gas is explosive, this method must be carried out in the presence of an excess of acetaldehyde, and a complicated reaction system is required so as to aboid such reactant-mixing proportions as lead to explosion. Another well-known method for producing peracetic acid comprises oxidizing acetaldehyde in an inert solvent at low temperature in the presence of a trace of a heavy metal salt catalyst to produce peracetic acid and AMP. In this method, the selectivity to peracetic acid may be improved by using a heavy metal salt in as extremely small an amount as less than 0.001% to acetaldehyde (British patent No. 864,803), but the oxidation rate is low and the selectivity to peracetic acid is hardly recognized to be high.

The object of this invention is, therefore, to provide a process for the production of peracetic acid wherein the formation reaction of AMP is controlled to increase the selectivity to peracetic acid.

By the symbol "pKa" used herein is meant the common logarithm of the reciprocal of the dissociation constant of an electrolyte. If the dissociation constant is taken to be "Ka", then the equation pKa = − log Ka results. The pKa valued used here are based on the Handbook of Chemistry complied by the Chemical Society of Japan published in 1966.

The term "sliphatic" used herein is intended to include alicyclics as well as aromatic compounds in which carbocylic groups are not directly connected to the aromatic ring.

The inventors carried out detailed research to find the most suitable catalyst to be used in the production of peracetic acid. They found that strongly acidic carboxylic acid or strongly acidic phenolic compound or nitric acid excell in catalystic action to produce peracetic acid in high selectively yield.

Among carboxylic acids having strong acidity below pKa 4.6 and soluble in the reaction solution, the following are chosen as the "strongly acidic carboxylic acids" which are effective catalysts, namely, formic acid, aliphatic polycarboxylic acids, aromatic polycarboxylic acids, aliphatic carboxylic acids having such functional groups as hydroxyl group, carbonyl group, amino group, halogen group, aldehyde group and ether linkage, and aromatic carboxylic acids having such functional groups as nitro group, hydroxyl group, aldehyde group and ether linkage.

Formic acid, aliphatic polycarboxylic acids, aromatic polycarboxylic acids, aliphatic carboxylic acids which have halogen group, hydroxyl group or carbonyl group, and aromatic carboxylic acids which have nitro group or hydroxyl group are especially effective. Each of these strongly acidic carboxylic acid catalysts is used singly or in combination with one or more others.

As the strong acidic phenols, phenols having more than two nitro groups or more than three halogen groups in the benzene nucleus, or other phenols having more than three strong electron withdrawal groups such as nitro group, halogen group and cyano groups are all useful, and the ones which contain more than three nitro groups are especially effective. These strongly acidic phenol compounds can be used singly, or in mixture of more than two, or together with strongly acidic carboxylic acids or nitric acid. However, phenol compounds act to suppress, more or less, the oxidation of acetaldehyde and the effect of suppression increases as the number of phenolic OH groups in the molecule increases. Therefore, it is not desirable for the phenols to have more than two phenolic OH groups when used singly and more than three of them when used in combination with heavy metal salt catalysts.

As for nitric acid, the concentrated nitric acid sold on the market can be used as it is. In general, one of more than 20% concentration is desirable, but it does not matter much if its concentration is higher or lower than said figure. It may be used together with strongly acidic carboxylic acid catalysts.

The effectiveness of these strongly acidic substances is chiefly related to the selectivity of peracetic acid and the increase in the rate of oxidation has not been generally recognized, and in the case of using them in a large quantity, the rate of oxidation is often lowered.

The comparison between the method of oxidation with strongly acidic carboxylic acid catalysts and that of non-catalytic oxidation is shown in Table I. This is the result of the experiments in which acetaldehyde was oxidized in the 15% acetone solution by oxygen at 20° C under normal pressure and the quantity of catalyst was 0.02 weight % based on the reaction solution.

Table 1

| Catalyst | Selectivity (based on oxygen reacted) at the point where oxygen equivalent to 20 mol % of acetaldehyde used reacted (%) | |
|---|---|---|
| | peracetic acid | AMP |
| tricholoroacetic acid | 100 | 0 |
| formic acid | 74 | 21 |
| lactic acid | 65 | 21 |
| pyruvic acid | 82 | 18 |
| glycine | 70 | 30 |

Table 1-continued

Selectivity (based on oxygen reacted) at the point where oxygen equivalent to 20 mol % of acetaldehyde used

| Catalyst | reacted (%) | |
|---|---|---|
| | peracetic acid | AMP |
| oxalic acid | 84 | 9 |
| malonic acid | 95 | 5 |
| fumaric acid | 70(at 25% conversion) | 24 |
| maleic acid | 74 | 21 |
| azelaic acid | 70(at 18% conversion) | 25 |
| cysteine | 66 | 27 |
| nitrilo triacetic acid | 83 | 17 |
| citric acid | 82 | 13 |
| 3.5-dinitro benzoic acid | 93 | 7 |
| 3.5-dinitro salicylic acid | 66 | 21 |
| 5-chloro salicylic acid | 86 | 14 |
| phthalic acid | 78 | 21 |
| Reference experiments: | | |
| none | 25 | 47 |
| acetic acid | 35 | 43 |

From this Table it is clear that when strongly acidic carboxylic acid is added, the selectivity of peracetic acid is 2.5 or more times higher than when no catalyst is used, but its selectivity varies depending on the kind of catalyst.

As a reference, the selectivity in the case where acetic acid (pKa = 4.76) used as catalyst is also shown in the table. In the case of acetic acid catalyst the selectivity of peracetic acid is a little higher than in the case of non-catalyst, but comparing with any acid below pKa 4.6 the catalytic effect was very much worse and when an other acid above pKa 4.6 (for example : propionic acid, iso-butyric acid, and naphthenic acid) was used as the catalyst, in no case has high selectivity of peracetic acid attained. On the other hand, as shown in Table 1, by the acid catalyst of this invention high selectivity of peracetic acid was attained and it is surprising that the catalytic activity of acids changes so distinctly at the point of pKa 4.6.

5.0 to 0.000001 weight % of the strongly acidic carboxylic acid catalyst based on the reaction solution can be used, but the preferred amount is between 0.1 and 0.001 weight %. If the amount is too large, the oxidation rate of acetaldehyde is lowered substantially, (for example; in the case of citric acid (10 weight %) or lactic acid (15 weight %) being added, the oxidation of acetaldehyde scarcely goes on) and the selectivity of peracetic acid somewhat goes down too, while, if its amount is too small, the effect of the catalyst can not be observed. The catalyst remains partly or completely dissolved in the reaction solution.

Table 2 shows the comparison between the oxidation by the strongly acidic phenol catalysts and the non-catalyst oxidation. In these experiments, acetaldehyde was oxidized in the 16% acetone solution by oxygen under normal pressure at 18° – 22° C. The amount of strongly acidic phenol catalyst used was 0.02 weight % based on the reaction solution.

Table 2

| | Maximum amount of absorbed oxygen per hour (mol % to acetaldehyde used) | Selectivity at 10%-conversion (%) (based on oxygen reacted) | | Selectivity at 20%-conversion (%) (based on oxygen reacted) | |
|---|---|---|---|---|---|
| | | peracetic acid | AMP | peracetic acid | AMP |
| 2,4,6-trinitro-phenol | 8 | 100 | 0 | 76 | 24 |
| 2,6-dinitro-phenol | 10 | 93 | 7 | 63 | 37 |
| 2,4-dinitro-phenol | 10 | 91 | 9 | 63 | 37 |
| pentachloro-phenol | 12 | 95 | 5 | 70 | 30 |
| 2,4,6-trichloro-phenol | 11 | 92 | 8 | 68 | 32 |
| 2,4,6-tribromo-phenol | 9 | 87 | 13 | 60 | 40 |
| Reference experiment: | | | | | |
| none | 15 | 30 | 70 | 28 | 62 |

The amount of the strongly acidic phenol catalyst to be used is 1.0 to 0.00001 weight % based on the reaction solution. But a more desirable amount is between 0.1 and 0.0005 weight %. If the amount is too large, the effect of suppressing the oxidation appears clearly, and the oxidation comes to be slow or completely stops. On the other hand, if the amount is too small, the effect of increasing the selectivity of peracetic acid can not be observed.

Table 3 shows the comparison between the nitric acid catalyst oxidation and, the non-catalyst oxidation. This is the result of the experiments in which acetaldehyde was oxidized by oxygen in the 20% acetone solution at 20° C under normal pressure. The amount of used nitric acid (60%) was 0.01 weight % based on the reaction solution.

Table 3

| | | Non catalyst | Nitric acid catalyst |
|---|---|---|---|
| Maximum amount of absorbed oxygen per hour (mol % to acetaldehyde used) | | 15 | 16 |
| Selectivity at 10%-conversion (%) (based on oxygen reacted) | peracetic acid | 30 | 100 |
| | AMP | 70 | 0 |
| Selectivity at 20%-conversion (%) (based on oxygen reacted) | peracetic acid | 28 | 95 |
| | AMP | 62 | 5 |
| Selectivity at 30%-conversion (%) (based on oxygen reacted) | peracetic acid | 30 | 85 |
| | AMP | 40 | 12 |
| Selectivity at 40%-conversion (%) (based on oxygen reacted) | peracetic acid | 12 | 70 |
| | AMP | 13 | 16 |

0.5–0.000001 weight % of nitric acid based on the reaction solution can be used, but the preferred amount is between 0.05 and 0.001 weight %. If the amount is too large, the rate of oxidation of acetaldehyde lowers remarkably, and so does the selectivity of peracetic acid. But if the amount is too small, the effect of selective formation of peracetic acid can not be observed.

The inventors, having further studied in detail the method of increasing the rate of reaction without lowering the selectivity of peracetic acid, came to find that if a little amount of heavy metal salt which can change its valency (for example: such soluble salts as iron, cobalt, manganese, nickel, copper, vanadium, chromium and others) is added to the reaction solution, together with the above-mentioned acidic catalysts, the rate of oxidation of acetaldehyde and the selectivity of peracetic acid both increase remarkably.

This method combining acidic catalysts and heavy metal catalysts is proved to give far higher selectivity of peracetic acid and far higher rate of oxidation of acetaldehyde, when compared with British patent No. 864,803 and other known methods for production of peracetic acid (liquid-phase oxidation of acetaldehyde).

Details of the catalysts mechanism have not been fully worked out, but probably the high selectivity of peracetic acid is due to the acidic catalyst components and the high rate of oxidation is due to the heavy metal catalyst components.

When more than 0.001% (based on the acetaldehyde used) of the heavy metal catalyst adopted in this invention is used alone, the decomposition of peracetic acid works strongly. (Japanese Pat. No. 441,391, etc.) and it is generally known that the increase in concentration of the heavy metal salt catalyst generally lowers the selectivity of peracetic acid. But it is suprising to find that, in the case of combining said metal catalyst with the acidic catalyst as in this invention, even if the concentration of the heavy metal salt component is above 0.001–5.0 weight % based on the acetaldehyde used, the metal component chiefly helps the rate of oxidation to increase and raises the selectivity of peracetic acid far higher than in the case of any other known methods.

As the strongly acidic carboxylic acid to be used in the method combining acidic catalyst and heavy metal catalyst, the following are chosen from carboxylic acids which have strong acidity below pKa 4.6 and are soluble in the reaction solution; aliphatic or aromatic polycarboxylic acids, aliphatic or aromatic carboxylic acid containing hydroxyl group, carbonyl group, halogen group, cyano group, amino group, nitro group, aldehyde group, ether linkage (inclusive of cyclic ether), or heterocyclic carboxylic acids of which the ring contains nitrogen or oxygen. They are all effective, but polycarboxylic acids below pKa 4.0 are especially effective. These strongly acidic carboxylic acids are each used singly or in combination of two or more. Most strong acids below pKa 4.6 may work as the effective catalyst in this reaction, but if any substitution group such as $NH_2$-group, OH-group or any other group that has the nature of inhibiting autoxidation reaction exists in the carboxylic acid molecule, the rate of oxidation lowers almost in proportion to the number of such groups in the molecule of carboxylic acid. The effect one suppressing the oxidation varies depending on the kinds of substitution groups, and as for the SH-group which has a strong inhibiting activity, the existence of only one group is strinkingly effective. But in the case of such groups as $NH_2$-group or OH-group which do not have a very strong inhibiting activity, more than two are actually needed for the acid molecule to retard the oxidation.

Oxalic acid and tartoronic acid, which are members of aliphatic polycarboxylic acids, are specific, and, for example, when they are used together with an ferric salt catalyst, the effect of the latter catalyst is lowered very much; that is, the oxidation rate is very poor. (Refer to Table 4.)

The scope of the strongly acidic phenol catalyst to be used in the method combining acidic catalyst and heavy metal salt catalyst is just the same as already mentioned in the part of its single-use method. Nitric acid catalyst may be added in the from of aqueous solution here, too, as in the case of its single-use method. These acidic catalysts (strongly acidic carboxylic acids, strongly acidic phenols and nitric acid) can be used singly or in combinations of two or more as in the case of the single-used acidic catalyst method.

As the heavy metal salts to be used in the method combining acidic catalyst and heavy metal salt catalyst, soluble salts of valency-variable metals such as iron, cobalt, nickel, manganese, copper, vanadium and chromiun are used, and iron-salt, cobalt-salt and manganese-salt are most suitable. They are each used singly or in combinations of two or more.

As the salt soluble in the reaction solution, the salts of aliphatic acids, naphthenates, benzoates, acetyl acetenates, nitrate and others are considered suitable. More generally speaking, these metallic ions are necessary to be supplied to the reaction solution, and any form of the salt may be used as long that principle is followed. Concerning the amount of the heavy metal salt to be used, 0.2 to 0.000001 weight % based on the reaction solution is suitable, but the preferred amount is 0.02–0.00001 weight %. If the amount is too large, the rate of decomposition of peracetic acid increases if the amount used is too small, the rate of the oxidation slowes down sharply.

The amount of the acidic catalyst to be used is the same as one mentioned in the single-use method of the acidic catalyst. Namely, it varies depending on the reaction conditions, but, in general, it varies depending on the reaction conditions, but, in general, in the case of strongly acidic carboxylic acid catalyst the amount is between 5.0 and 0.000001 weight % (the preferred amount is between 0.1 and 0.001 weight %) based on the reaction solution. Again, in the case of the strongly acidic phenol catalyst, 1.0 to 0.00001 weight % based on the reaction solution is suitable (the preferred amount is between 0.1 and 0.0005 weight %). In the case of nitric acid catalyst, 0.5 to 0.000001 weight % based on the reaction solution is suitable, but the preferred amount is between 0.05 and 0.001 weight %. If the amount of these acidic catalysts is too large, the rate of oxidation of acetaldehyde lowers and the selectivity of peracetic acid somewhat comes down. On the other hand, if the amount is too small, the selectivity of peracetic acid comes down.

The amount of the acidic catalyst and the heavy metal salt catalyst to be used may be changed within the range abovementioned, but if the amount of the acidic catalyst used is too small to that of the heavy metal salt catalyst, the effect of the acidic catalyst to increase the selectivity of peracetic acid disappears. In some cases, the effect on the heavy metal salt catalyst to promote acetaldehyde oxidation decreases very much. On the other hand, if the proportion of the acidic catalyst is too large, the rate of oxidation lowers.

Generally speaking, the most desirable ratio in using these two components of catalyst is about one to six molecules of the acidic catalysts to 1 atom of metal in the heavy metal salt catalyst used. The catalyst remains partly or completely dissolved in the reaction solution.

Comparing the method combining acidic catalyst and heavy metal salt catalyst with the ceses where no acidic catalyst is used, it is clear that the former produces peracetic acid more effectively and in higher selectivity, as shown in Tables 4–10. The values shown in these tables are, of course, not those taken under optimum conditions for the individual catalyst-systems. As mentioned fully in this paper, there is no need to say that by changing the reaction conditions, higher selectivity of peracetic acid may be attained in some cases.

Table 4 shows the results of the experiments in which acetaldehyde was oxidized by oxygen at 18°–22° C under normal pressure for one hour in the 15% aceton solution containing 0.02 weight % based on the reaction solution of ferric naphthenate and 0.02 weight %, based on the reactant solution, of strongly acidic carboxylic acid catalyst. Besides, as reference experiments, the results of an experiment not using an acidic catalyst and another experiment using acetic acid (0.02 weight %) are also shown.

Table 5 shows the results of the experiments in which 0.02 weight %, based on the reaction solution, of pyromellitic acid as the strongly acidic carboxylic acid and 0.02 weight % based on the reaction solution, of various heavy metal naphthenate were added, the other conditions being the same as those in Table 4.

Table 6 shows the results of one hour's reaction in which, under the pressure of 100 mm Hg (gauge) and at the same temperature as in Table 4, acetaldehyde was oxidized in the 15% aceton solution containing 0.02 weight %, based on the reaction solution, of malonic acid as the strongly acidic acid catalyst and 0.02 weight %, based on the reaction solution, of various heavy metal naphthenates.

Table 7 shows the results of the experiments in which acetaldehyde was oxidized by oxygen under normal pressure at 18° C to 22° C for half an hour in the 16% aceton solution containing 0.02 weight %, based on the reaction solution, of ferric naphthenate catalyst and 0.02 weight %, based on the reaction solution, of various strongly acidic phenol catalysts.

Table 8 shows the comparison of the results of the experiments in which 0.02 weight %, based on the reaction solution, of various kinds of metallic naphthenate catalyst was used under the same conditions as in Table 7 with the exception that the reaction time was one hour, with those of the experiments in which 0.02 weight %, based on the reaction solution, of 2,4,6-trinitroresorcinol was used as an additional catalyst. (The experiment using manganese salt alone showed that the rate of formation of decomposed gas was so high that the oxidation could not smoothly progress.)

Table 9 shows the difference in detail between the case in which 2,4,6-trinitroresorcinol, which is very effective as the strongly acidic phenol catalyst, was used alone and the case in which ferric naphthenate is used together with the said strongly acidic phenol. In these cases the experimental conditions were also just the same as in the cases of Table 7 and 8.

Table 10 shows the results of the experiments of the method combining nitric acid and heavy metal salt catalyst. Namely, when 20% acetone solution of acetaldehyde was oxidized by oxygen under normal pressure at 18°-22° C for 1 hour, the amount of heavy metal naphthenate corresponding to $1 \times 10^{-4}$g atom of metal to 1 mol of acetaldehyde used and $3 \times 10^{-4}$mol of nitric acid based on 1 mol of used acetaldehyde were added as the catalysts. When manganese salt catalyst was singly used, its rate of fromation of decomposed gas was so large that further oxidation experiment could not be carried on in this reaction apparatus, but if said catalyst was used together with nitric acid catalyst, peracetic acid could be formed in high yield.

Table 10 also shows the results of a reference experiment in which ferric nitrate containing the same amount of iron as in the experiment using ferric naphthenate plus nitric acid is added as catalyst. The catalytic activity was found to be worse than in the experiment using ferric naphthenate plus nitric acid, and the effect of the combined catalyst system, heavy metal salt plus nitric acid, proved not to have resulted from the formation of heavy metal nitrate.

Table 4

| Method combining ferric naphtenate catalyst and strongly acidic carboxylic acid catalyst | | | |
|---|---|---|---|
| Strongly acidic carboxylic acid catalyst | Amount of absorbed oxygen (mol % to acetaldehyde used) | Selectivity (%) (based on oxygen reacted) | |
| | | peracetic acid | AMP |
| trichloro acetic acid | 41 | 58 | 33 |
| dl-α-amino-n-butyric acid | 57 | 49 | 28 |
| pyruric acid | 40 | 38 | 39 |
| salicylic acid | 38 | 48 | 34 |
| anthranilic acid | 39 | 46 | 25 |
| 2,4-dichlorobenzoic acid | 49 | 40 | 43 |
| O-acetamidobenzoic acid | 42 | 35 | 35 |
| 3,5-dinitrobenzoic acid | 46 | 57 | 25 |
| fumaric acid | 46 | 92 | 8 |
| malonic acid | 42 | 69 | 16 |
| succinic acid | 42 | 48 | 33 |
| azelaic acid | 43 | 40 | 40 |
| maleic acid | 38 | 90 | 7 |
| L-gulutamic acid | 60 | 56 | 25 |
| oxalic acid | 16 | 75 | 20 |
| oxalic acid* | 62 | 51 | 30 |
| phthalic acid | 48 | 70 | 20 |
| hexahydrophthalic acid | 63 | 54 | 25 |
| naphthalene-1.8-dicarboxylic acid | 51 | 76 | 20 |
| citric acid | 53 | 100 | 0 |
| pyromellitic acid | 64 | 95 | 5 |
| furan carboxylic acid | 47 | 46 | 36 |
| picolinic acid | 45 | 38 | 40 |
| nicotinic acid | 67 | 58 | 18 |
| cysteine | 56 | 50 | 32 |
| acetylene dicarboxylic acid | 65 | 90 | 10 |
| β-ketoglutaric acid | 42 | 82 | 15 |
| tartoronic acid | 21 | 97 | 3 |
| oxalacetic acid | 42 | 100 | 0 |

Table 4-continued

Method combining ferric naphtenate catalyst and strongly acidic carboxylic acid catalyst

| Strongly acidic carboxylic acid catalyst | Amount of absorbed oxygen (mol % to acetaldehyde used) | Selectivity (%) (based on oxygen reacted) | |
|---|---|---|---|
| | | peracetic acid | AMP |
| 4-hydroxyisophthalic acid | 33 | 70 | 22 |
| acetyl glycine | 63 | 53 | 29 |
| glycolic acid | 69 | 60 | 22 |
| cyano-acetic acid | 48 | 45 | 37 |
| 1,2,4-benzene tricarboxylic acid | 59 | 98 | 2 |
| nitriloriacetic acid | 54 | 47 | 34 |
| imino diacetic acid | 56 | 44 | 41 |
| Reference experiments: | | | |
| none | 37 | 26 | 44 |
| acetic acid | 36 | 27 | 47 |

(*Instead of ferric naphthenate the same weight of cobalt naphthenate was used.)

Table 5

Method combining pyromellitic acid catalyst and heavy metal naphthanate catalyst

| Heavy metal naphthenate catalyst | Amount of absorbed oxygen (mol % to acetaldehyde used) | Selectivity (%) (based on oxygen reacted) | |
|---|---|---|---|
| | | peracetic acid | AMP |
| ferric- | 64 | 95 | 5 |
| cobalt- | 68 | 91 | 8 |
| manganese- | 69 | 92 | 6 |
| nickel- | 32 | 75 | 22 |
| copper- | 28 | 65 | 20 |
| vanadium- | 27 | 77 | 20 |
| chromium- | 27 | 79 | 16 |
| Reference experiment: | | | |
| none | 14 | 100 | 0 |

Table 6

Method combining malonic acid catalyst and heavy metal naphthenate catalyst

| Heavy metal naphthenate catalyst | Amount of absorbed oxygen (mol % to acetaldehyde used) | Selectivity (%) (based on oxygen reacted) | |
|---|---|---|---|
| | | peracetic acid | AMP |
| ferric- | 59 | 88 | 12 |
| cobalt- | 62 | 86 | 12 |
| manganese- | 62 | 86 | 9 |
| nickel- | 30 | 77 | 21 |
| chromium- | 28 | 81 | 17 |
| Reference experiment: | | | |
| none | 23 | 92 | 8 |

Table 7

Method combining ferric naphthenate catalyst and strongly acidic phenol catalyst

| Strongly acidic phenol catalyst | Amount of absorbed oxygen (mol % to acetaldehyde used) | Selectivity (%) (based on oxygen reacted) | |
|---|---|---|---|
| | | peracetic acid | AMP |
| 2,4,6-trinitroresorcinol | 55 | 83 | 14 |
| 2,4,6-trinitrophenol | 56 | 86 | 14 |
| 2,6-dinitrophenol | 41 | 65 | 25 |
| 2,4-dinitrophenol | 40 | 59 | 29 |
| pentachlorophenol | 39 | 64 | 31 |
| 2,4,6-trichlorophenol | 38 | 60 | 31 |
| Reference experiment: | | | |
| none | 50 | 48 | 32 |

Table 8

| Naphthenate catalyst | Amount of absorbed oxygen (mol % to acetaldehyde used) | Selectivity (%) (based on oxygen reacted) | |
|---|---|---|---|
| | | peracetic acid | AMP |
| ferric- | 59 | 45 | 34 |
| ferric-* | 70 | 80 | 14 |
| cobalt- | 59 | 49 | 43 |
| cobalt-* | 69 | 82 | 14 |
| manganese-* | 71 | 78 | 15 |
| nickel- | 28 | 19 | 71 |
| nickel-* | 32 | 69 | 28 |
| copper- | 25 | 19 | 76 |
| copper-* | 27 | 63 | 20 |
| vanadium- | 23 | 19 | 69 |
| vanadium-* | 27 | 70 | 25 |
| chromium- | 24 | 20 | 73 |
| chromium-* | 26 | 74 | 20 |

(marked * indicates experiments in which 2,4,6-trinitroresorcinol was used as an additional used as catalyst)

Table 9

| Catalyst | | ferric naphthenate | Ferric naphthenate + 2,4,6-trinitroresorcinol | Ferric naphthenate + 2,4,6-trinitrophenol |
|---|---|---|---|---|
| Maximum amount of absorbed oxygen per hour (mol % to acetaldehyde used) | | 59 | 70 | 63 |
| Selectivity at 20%-conversion (%) (based on oxygen reacted) | peracetic acid | 66 | 100 | 100 |
| | AMP | 34 | 0 | 0 |
| Selectivity at 40%-conversion (%) (based on oxygen reacted) | peracetic acid | 50 | 85 | 90 |
| | AMP | 38 | 15 | 10 |
| Selectivity at 60%-conversion (%) (based on oxygen | peracetic acid | 47 | 82 | 78 |

Table 9-continued

| Catalyst | | ferric naphthenate | Ferric naphthenate + 2,4,6-trinitroresorcinol | Ferric naphthenate + 2,4,6-trinitrophenol |
|---|---|---|---|---|
| reacted) | AMP | 26 | 12 | 13 |

Table 10

| Catalyst (naphthenate and/or nitric acid) | Amount of absorbed oxygen (mol % to acetaldehyde used) | Selectivity (%) (based on oxygen reacted) | |
|---|---|---|---|
| | | peracetic acid | AMP |
| iron | 55 | 45 | 37 |
| iron + nitric acid | 72 | 85 | 15 |
| cobalt | 50 | 48 | 45 |
| cobalt + nitric acid | 73 | 85 | 15 |
| manganese + nitric acid | 68 | 82 | 17 |
| nickel | 28 | 19 | 71 |
| nickel + nitric acid | 30 | 72 | 26 |
| copper | 24 | 19 | 76 |
| copper + nitric acid | 27 | 63 | 20 |
| vanadium | 23 | 18 | 71 |
| vanadium + nitric acid | 27 | 74 | 23 |
| chromium | 23 | 20 | 73 |
| chromium + nitric acid | 27 | 76 | 19 |
| Reference experiment: ferric nitrate | 57 | 67 | 22 |

The effect of the method combining acidic catalyst and metal salt catalyst of this invention is not due to the formation of salts (except acid salts) of the acidic catalyst in the reaction of the acidic catalyst and the heavy metal salt. This was made clear in comparison with the results of the experiments in which the corresponding salt was used as the catalyst.

The inventors further studied on the method combining acidic catalyst and heavy metal catalyst and found that the soluble acid salts composed of the above-mentioned heavy metal as the metal component and the strongly acidic polycarboxylic acid below pKa 4.0 or the above-mentioned strongly acidic phenol containing two phenolic OH groups as the acid component bring forth, effects similar to those in the case in which the above said acidic catalyst and the heavy metal salt catalyst are used together, that is, the high selectivity of peracetic acid and the high rate of oxidation of acetaldehyde.

As the acid component of the acid salt catalyst, the polycarboxylic acids below pKa 4.0 and strongly acidic dibasic phenols used in the above-mentioned method combining acidic catalyst and the heavy metal catalyst can all be adopted.

The amount of acid salt catalyst to be added differs depending on the reaction conditions, but, in general, it is 0.2–0.000001 weight % (as metal) based on the reaction solution, preferably 0.02–0.00001 weight %. When the concentration of the catalyst is too high in the reaction solution, the rate of decomposition of peracetic acid increases, and the selectivity of peracetic acid goes down. On the other hand, said concentration is too low, the effect of the catalyst can not be recognized.

The comparative examples between the cases in which the acid salt catalyst of carboxylic acid was used and the cases in which the heavy metal salt was used are shown in Tables 11 and 12. The results of the method using a monophenolate catalyst was shown in Example 37. The date in these tables are, of course, not the results of each catalyst system under optimum conditions, and, as fully mentioned here, by changing the reaction conditions it is naturally possible in some cases to achieve far higher selectivity of peracetic acid than in the tables. Table 11 shows the results of the experiments in which a 16% acetone solution of acetaldehyde was oxidized by oxygen at 18°–22° C under normal pressure by using naphthenates or acid pyromellitates of various heavy metals equivalent to $1 \times 10^{-4}$ gram atom of the metal per 1 mol of the acetaldehyde used as the catalyst.

Table 12 shows the results of the experiments in which acid ferric salts of various polycarboxylic acids were used as the catalyst. Methods of producing the acid salts of polycarboyxlic acids are widely known among those skilled in the art; for example, a method in which newly produced hydroxide of heavy metal is added to a heated concentrated aqueous solution of polycarboxylic acid or the method in which sodium hydrogen salt of polycarboxylic acid is reacted with nitrate of heavy metal is adopted. In the reaction solution, the catalysts were found partly or completely dissolved.

Table 11

| Catalyst | Maximum amount of absorbed oxygen per hour (mol % to acetaldehyde used) | Selectivity at 20%-conversion (%) (based on oxygen reacted) | | Selectivity at 40%-conversion (%) (based on oxygen reacted) | |
|---|---|---|---|---|---|
| | | peracetic acid | AMP | peracetic acid | AMP |
| iron | 59 | 66 | 34 | 50 | 38 |
| iron* | 21 | 100 | 0 | 100 | 0 |
| cobalt | 59 | 69 | 31 | 52 | 41 |
| cobalt* | 52 | 100 | 0 | 100 | 0 |
| nickel | 28 | 25 | 73 | 15 | 3 |
| nickel* | 22 | 85 | 15 | 55 | 12 |
| copper | 25 | 23 | 77 | 11 | 6 |
| copper* | 19 | 72 | 18 | 38 | 4 |
| chromium | 24 | 24 | 74 | 17 | 16 |
| chromium* | 21 | 80 | 20 | 59 | 7 |
| Reference experiment: pyromellitic | | | | | |

Table 11-continued

| Catalyst | Maximum amount of absorbed oxygen per hour (mol % to acetaldehyde used) | Selectivity at 20%-conversion (%) (based on oxygen reacted) | | Selectivity at 40%-conversion (%) (based on oxygen reacted) | |
|---|---|---|---|---|---|
| | | peracetic acid | AMP | peracetic acid | AMP |
| acid only | 14 | 100 | 0 | 75 | 16 |

Note 1:The catalysts with an asterisk indicate the acidic pyromellitate while the others are naphthenates.
Note 2:In the reference experiment the same amount of pyromellitic acid as the acid component of the acidic pyromellitate catalyst in other experiments.
Note 3:Acid salts of pyromellitic acid were produced by adding newly-produced heavy metal hydroxide to the surplus 10% aqueous solution of pyromellitic acid heated at 90° – 100° C.

Table 12

| Catalyst (carboxylic acid component) | Maximum amount of absorbed oxygen per hour (mol % to acetaldehyde used) | Selectivity at 20%-conversion (%) (based on oxygen reacted) | | Selectivity at 60%-conversion (%) (based on oxygen reacted) | |
|---|---|---|---|---|---|
| | | peracetic acid | AMP | peracetic acid | AMP |
| malonic acid | 54 | 100 | 0 | 86 | 12 |
| maleic acid | 62 | 100 | 0 | 96 | 4 |
| fumaric acid | 42 | 73 | 27 | 57 | 29 |
| tartoronic acid | 56 | 100 | 0 | 100 | 0 |
| hexahydro-phthalic acid | 69 | 95 | 5 | 87 | 13 |
| phthalic acid | 80 | 100 | 0 | 93 | 7 |
| trimellitic acid | 65 | 100 | 0 | 90 | 10 |
| Reference experiments: | | | | | |
| naphthenic acid | 59 | 65 | 35 | 42 | 10 |
| trichloro acid | 53 | 66 | 34 | 39 | 12 |
| phthalic acid | 49 | 88 | 12 | 60 | 13 |
| | | | | (50%-conversion) | |

Note 1:Among the acid salts mentioned in this table, those of maleic acid, fumaric acid, and tartaronic acid were made by the same method as in the case of the acid salt of pyromellitic acid in Table 11. The acid salts of malonic acid, hexahydro-phthalic acid, phthalic acid, and trimellitic acid were made by the method in which one mole of sodium hydrogen carbonate is added to the polycarboxylic acid (one mole) aqueous solution to form the acidic sodium salt of polycarboxylic acid and then ⅓ mole of ferric nitrate is added thereto.
Note 2:The solubility of the salt of fumaric acid was poor and a part of it remained undissolved. The other kinds of salts were all dissolved in the reaction solution.
Note 3:In the reference experiment the equal amount of iron to that in the case of acid salt was added as normal salt.

After further studies on the method combining heavy metal salt catalyst and acidic catalyst, the inventors found that the combined catalyst system of a normal salt of a heavy metal of which the acid component was the acidic acid catalyst and a strong acid which did not belong to the acidic catalyst in the invention, for example, hydrochlonic acid, often showed similar effects to those of the combined system of acidic catalyst and heavy metal salt catalyst. The inventors had the idea that, in order to obtain peracetic acid in high selectivity as well as to obtain high oxidation rate, the coexistence of an acidic catalyst and a heavy metal ion or an acid salt composed of these two components would be necessary. According to this idea, it may be reasonably understood that the said method combining the heavy metal salt of the acidic catalyst plus the strong acid not belonging to the acidic catalyst is effective.

Namely, for example, the heavy metal salt of the acidic catalyst may react with hydrochloric acid to form the acidic catalyst and metal chloride or the acid salt of the acidic catalyst in the reaction liquid. But, as the concentration of the catalyst and the reaction temperature are low under oxidation conditions, the said combined catalyst system gives little amouts of soluble effective catalyst components in some cases, then high activity is not expected there.

To say little more detail, the heavy metal salt of strongly acidic monocarboxylic acid, of strongly acidic monophenol, or of nitric acid accompanied by a theoretical or a little larger amount of hydrogen chloride or hydrochloric acid showed similar effects to those of the combined catalyst-system of the corresponding acidic catalyst and the heavy metal salt.

In this "heavy metal salt of the acidic catalyst plus hydrogen chloride" system, the amount of the salt catalyst of which the amount of the metal component is in the same range as that in the said "acidic catalyst plus heavy metal salt catalyst" system can be used. When the amount of hydrogen chloride used is too small comparing with the amount of heavy metal salt used, effective acidic catalyst can not be sufficiently formed, while the amount of hydrogen chloride several times as much as that of the metal salt shows no undesirable effect whatever on the oxidation, as shown in the examples.

As the inert solvent in the invention, acetates having less than seven carbon atoms, ketones having less than seven carbon atoms, hydrocarbons, chlorohydrocarbons, etc. are used singly or in a mixture of more than two of them, and said esters of acetic acid and said ketones are the most suitable. If the catalyst can be dissolved, the solvent containing some water may be used, but the large content of water results in decrease of both the rate of oxidation and the selectivity of peracetic acid. Regarding the ratio of solvent to acetaldehyde, if it is too low, the yield of peracetic acid decreases, and, if said ratio is too high, the rate of oxidation decreases. Generally speaking, 2 to 10 parts by weight of the solvent is preferred to 1 part of the acetaldehyde used.

As for the reaction temperature, −5° C to 50° C, especially 0° C to 35° C, is desirable. If the temperature is too low, the rate of oxidation becomes low, and, if the temperature is too high, the decomposition of peracetic acid becomes great and the yield of peracetic acid comes down. As the oxidizer gas, oxygen gas or oxygen containing gas, for example, air is used under normal or a little higher pressure. With the increase in partial pressure of oxygen, the rate of oxidation and the yield of peracetic acid increase. Therefore, in the case of using air as the oxidizer gas or using the acidic catalyst alone, it is desirable to carry out the oxidation under pressure.

The use of ultraviolet ray radiation or the addition of a small amount of ozone increases the rate of oxidation, and some increase of the selectivity of peracetic acid may be then expected.

The methods of the invention may be put to work either batchwise or in flow system. The separation of peracetic acid from the product can be effected by the methods which are widely known to the specialists in this field. The reaction liquid as it is or the part of the reaction solution remaining after distilling out the unreacted acetaldehyde alone or after distilling out unreacted acetaldehyde and most of the solvent may be used as the oxidizer without purification.

DESCRIPTION OF PREFERRED EMBODIMENTS:

The following Examples are further illustrative of this invention, and it will be understood that the invention is not limited thereto.

EXAMPLE 1

A 500 ml four-neck flask equipped with a stirrer, a reflux condenser (kept at −50° C), a thermometer and a gas blowing inlet was charged with 25g of acetaldehyde, 80g of acetone and 0.005of 0.005g acid. Oxygen gas was then introduced into the flask at a rate of 350 ml per minute while vigorously stirring the solution at a rate of 700 r.p.m. and maintaining the reaction temperature at 25° C to 30° C. The gas discharging from the reflux condenser was recycled to the reaction system by means of a recycle pump while supplying fresh oxygen to compensate the amount absorbed. After 1.5 hours' reaction, the reaction solution was analyzed, showing that it contained 16.8g of unreacted acetaldehyde, 11.9g of peracetic acid and 1.7g of AMP and that acetic acid was almost not produced.

EXAMPLE 2

The reaction system employed in Example 1 was charged with 24g of acetaldehyde, 126g of acetone, 0.04g of trichloroacetic acid and 0.01g of 3.5-dinitrobenzoic acid. Oxygen gas was then introduced into the flask under the pressure of 150 mm Hg (gauge) at a rate of 300 to 400 ml per minute while vigorously stirring the solution at a rate of 900 r.p.m. and maintaining the reaction temperature at 20° C to 22° C. After 2 hours' reaction, the reaction solution was analyzed, showing that it contained 16.7g of unreacted acetaldehyde, 11.4g of peracetic acid and 1.0g of AMP and that acetic acid was almost not produced.

EXAMPLE 3

In the reaction system used in Example 1, the flask was replaced by a 1500 ml four-neck flask, which was charged with 44g of acetaldehyde and 310g of ethyl acetate. A catalyst mixture of 0.02g of formic acid, 0.005g of oxalic acid, 0.1g of 3.5-dinitrosalicyclic acid and 0.2g of nitrilotriacetic acid was added to the reaction solution immediately after the lapse of the induction period of the reaction, and oxygen gas was introduced into the flask at a rate of 300 to 400 ml per hour while vigorously stirring the solution at a rate of 900 r.p.m. and maintaining the reaction temperature at 10° C to 15° C. After one hour from the time the catalyst was added, the reaction solution was analyzed, showing that it contained 35.8g of unreacted acetaldehyde, 9.7g of peracetic acid and 3.6g of AMP and that acetic acid was almost not produced.

EXAMPLE 4

A 200 ml autoclave equipped with a stirrer, a reflux condenser, a thermometer and a gas blowing inlet was charged with 20g of acetaldehyde, 100 g of acetone and 0.003g of citric acid. Oxygen gas was then introduced into the autoclave under a pressure of 3 kg/cm$^2$ (gauge) while vigorously stirring the solution at a rate of 500 r.p.m. and maintaining the reaction temperature at 15° C to 20° C. The induction period of this reaction was 30 minutes. After 30 minutes from the lapse of the induction period, the reaction solution was analyzed, showing that it contained 17.4g of unreacted acetaldehyde, 3.7g of peracetic acid and 0.6g of AMP and that acetic acid was almost not produced.

EXAMPLE 5

The reaction system employed in Example 4 was charged with 24g of acetaldehyde, 50g of acetone, 40g of methyl acetate, 0.02g of phthalic acid and 0.005g of pyruvic acid. Oxygen gas was then introduced into the autoclave under a pressure of 3 kg/cm$^2$ (gauge) while vigorously stirring the solution at a rate of 500 r.p.m. and maintaining the reaction temperature at 15° C to 20° C. After one hour's reaction, the reaction solution was analyzed, showing that it contained 15.5g of unreacted acetaldehyde, 1.9g of acetic acid, 7.3g of peracetic acid and 4.0g of AMP.

EXAMPLE 6

In the reaction system used in Example 1, the reflux condenser was kept at −78° C and the flask was charged with 44g of acetaldehyde, 120g of acetone and 20g of acetone dissolving 0.01g of 2,4,6-trinitrophenol. Oxygen gas was then introduced into the flask under the pressure of 150mm Hg (gauge) at a rate of 300 to 400 ml per minute while vigorously stirring the solution at a rate of 900 r.p.m. and maintaining the reaction temperature at 24° C to 27° C. After 1 hour and half from the lapse of the induction period, the reaction solution was analyzed, showing that it contained Lb 35.6g of unreacted acetaldehyde, 11.4g of peracetic acid and 2.4g of AMP and that acetic acid was almost not produced.

EXAMPLE 7

The reaction system employed in Example 4 was charged with 10g of acetaldehyde, 100g of acetone, 0.001g of 2,4-dinitro phenol and 0.001g of pentachlorophenol. Oxygen gas was then introduced into the autoclave under a pressure of 2 kg/cm$^2$ (gauge) while vigorously stirring the solution at a rate of 700 r.p.m. and maintaining the reaction temperature at 15° C to 20° C. After 2 hours' reaction, the reaction solution was analyzed, showing that it contained 6.2g of unreacted acetaldehyde, 3.5g of peracetic acid and 2.3g of AMP and that acetic acid was almost not produced.

EXAMPLE 8

The reaction system employed in Example 6 was charged with 20g of acetaldehyde, 100g of ethyl acetate and 0.007g of high-grade nitric acid (60% aqueous solution). Oxygen gas was then introduced into the flask at a rate of 350 ml per minute while vigorously stirring the solution at a rate of 900 r.p.m. and maintaining the reaction temperature at 30° C to 35° C. After 1.5 hours' reaction, the reaction solution was analyzed, showing that it contained 15.3g of unreacted acetaldehyde, 6.9g of peracetic acid and 0.9g of AMP and that acetic acid was almost not produced.

EXAMPLE 9

The reaction system employed in Example 4 was charged with 20g of acetaldehyde, 100g of acetone and 0.01 g of high-grade nitric acid (30% aqueous solution). Oxygen gas was then introduced into the autoclave under the pressure of 2kg/cm$^2$ (gauge) while vigorously stirring the solution at a rate of 700 r.p.m. and maintaining the reaction temperature at 15° C to 20° C. After one hour's reaction, the reaction solution was analyzed, showing that it contained 13.0g of unreacted acetaldehyde, 10.4g of peracetic acid and 1.3g of AMP and that acetic acid was almost not produced.

EXAMPLE 10

The reaction system employed in Example 6 was charged with 20g of acetaldehyde, 70g of acetone, 10g of methyl ethyl ketone, 0.01g of citric acid and 0.01g of ferric naphthenate. Oxygen gas was then introduced into the flask at a rate of 300 to 400 ml per minute while vigorously stirring the solution at a rate of 700 r.p.m. and maintaining the reaction temperature at 25° C to 30° C. After 40 minutes' reaction, the reaction solution was analyzed, showing that it contained 7.2g of unreacted acetaldehyde, 20.4g of peracetic acid and 1.4g of AMP and that acetic acid was almost not produced.

Ferric naphthenate used above was prepared by adding an aqueous solution of ferric nitrate to and aqueous solution of sodium naphthenate and washing the formed precipitates with water. The iron content in the resulting naphthenate was 10.2%.

EXAMPLE 11

The reaction system employed in Example 6 was charged with 15g of acetaldehyde, 75g of ethyl acetate, 75g of methyl ethyl ketone, 0.001g of manganese naphthenate, 0.001g of cobalt naphthenate, 0.001g of oxalic acid and 0.001g of pyromellitic acid. Oxygen gas was then introduced into the flask at a rate of 300 to 400 ml per minute while vigorously stirring the solution at a rate of 900 r.p.m. and maintainging the reaction temperature at 10° C to 12° C. After 3 hours' reaction, the reaction solution was analyzed, showing that it contained unreacted acetaldehyde, in an amount less than 0.5g, 1.0g of acetic acid, 22.5g of peracetic acid and 1.3g of AMP.

The manganese naphthenate and cobalt naphthenate were prepared in the same manner as in the case of the iron naphthenate used in Example 10. The metal content in each naphthenate was about 10%.

EXAMPLE 12

The reaction system employed in Example 6 was charged with 24g of acetaldehyde, 116g of acetone, 10g of methyl ethyl ketone, 0.015g of ferric naphthenate, 0.01g of fumaric acid and 0.01g of trichloroacetic acid. Oxygen gas was then introduced into the flask under the pressure of 150 mm Hg (gauge) at a rate of 300 to 400 ml per minute while vigorously stirring the solution at a rate of 900 r.p.m. and maintaining the reaction temperature at 20° C to 22° c. After one hour's reaction, the reaction solution was analyzed, showing that it contained 7.7g of unreacted acetaldehyde, 23.5g of peracetic acid and 2.9g of AMP and that acetic acid was almost not produced.

EXAMPLE 13

In the reaction system used in Example 6, the flask was replaced by a 1500 ml four-neck flask, which was charged with 40g of acetaldehyde, 310g of acetone, 0.03g of cobalt acetate and 0.05g of phthalic acid. Oxygen gas was then introduced into the flask at a rate of 300 to 400 ml per minute while vigorously stirring the solution at a rate of 900 r.p.m. and maintaining the reaction temperature at 15° C to 20° C. After one hour's reaction, the reaction solution was analyzed, showing that it contained 25.0g of unreacted acetaldehyde and 26.0g of peracetic acid and that acetic acid and AMP were almost not produced.

EXAMPLE 14

The reaction system employed in Example 13 was charged with 60g of acetaldehyde, 300g of acetone, 100g of methyl acetate, 100g of methyl ethyl ketone, 0.01g of ferric naphthenate, 0.01g of chromium naphthenate, 0.01g of nickel naphthenate, 0.01g of maleic acid, 0.01g of succinic acid and 0.01g of hexahydrophthalic acid. Oxygen gas was then introduced into the flask under the pressure of 200 mm Hg (gauge) at a rate of 500 to 600 ml per minute while vigorously stirring the solution at a rate of 900 r.p.m. and maintaining the reaction temperature at 24° C to 26° C. After 1.5 hours' reaction, the reaction solution was analyzed, showing that it contained 9.0g of unreacted acetaldehyde, 78.0g of peracetic acid, 5.5g of AMP and 2.5g of acetic acid.

EXAMPLE 15

The reaction system employed in Examfple 6 was charged with 40g of acetaldehyde, 100g of acetone, 20g of methyl ethyl ketone, 0.01g of ferric acetonylacetonate, 0.01g of cobalt naphthenate and 0.01g of naphthalene-1,8-dicarboxylic acid. Oxygen gas was then introduced into the flask at a rate of 400 to 500 ml per minute while vigorously stirring the solution at a rate of 700 r.p.m. and maintaining the reaction temperature at 5° C to 10° C. After 40 minutes' reaction, the reaction solution was analyzed, showing that it contained 17.5g of unreacted acetaldehyde, 37.7g of peracetic acid and 1.2g of AMP and that acetic acid was almost not produced.

EXAMPLE 16

The reaction system employed in Example 13 was charged with 88g of acetaldehyde, 440g of methyl acetate, 0.05g of ferric acetonylacetonate, 0.05g of cobalt acetate, 0.01g of vanadium naphthenate, 0.1g of pyromellitic acid and 0.1g of L-gulutamic acid. Oxygen gas was then introduced into the flask under the pressure of 150 mm Hg (gauge) at a rate of 600 to 700 ml per minute while vigorously stirring the solution at a rate of 900 r.p.m. and maintaining the reaction temperature at 10° C to 12° C. After one hour's reaction, the reaction solution was analyzed, showing that it contained 28.0g of unreacted acetaldehyde, 99.5g of peracetic acid and 3.2g of AMP and that acetic acid was almost not produced.

EXAMPLE 17

A 300 ml autoclave equiped with a stirrer, a reflux condenser, a thermometer and a gas blowing inlet was charged with 10g of acetaldehyde, 100g of acetone, 0.001g of ferric acetate and 0.001g of malonic acid. Oxygen gas was then introduced into the autoclave under the pressure of 2kg/cm$^2$ (gauge) while vigorously stirring the solution at a rate of 500 r.p.m. and maintaining the reaction temperature at 15° C to 20° C. After 30 minutes' reaction, the reaction solution was analyzed, showing that it contained 5.1g of unreacted acetaldehyde, 7.2g of peracetic acid and 1.0g of AMP and that acetic acid was almost not produced.

EXAMPLE 18

The reaction system employed in Example 17 was charged with 20g of acetaldehyde, 120g of ethyl acetate, 0.03g of cobalt naphthenate and 0.04g of citric acid. Oxygen gas was then introduced into the autoclave under the pressure of 2kg/cm$^2$(gauge) while vigorously stirring the solution at a rate of 600 r.p.m. and maintaining the reaction temperature at 15° C to 20° C. After 30 minutes' reaction, the reaction solution was analyzed, showing that it contained 6.5g of unreacted acetaldehyde, 21.6g of peracetic acid and 1.4g of AMP and that acetic acid was almost not produced.

EXAMPLE 19

The reaction system employed in Example 17 was charged with 20g of acetaldehyde, 60g of ethyl acetate, 60g of methyl ethyl ketone, 0.01g of ferric naphthenate, 0.02g of nickel naphthenate, 0.03g of pyromellitic acid and 0.01g of maleic acid. Air was then introduced into the autoclave under the pressure of 8 kg/cm$^2$ at a rate of 500 ml per minute while vigorously stirring the solution at a rate of 600 r.p.m. and maintaining the reaction temperature at 15° C to 20° C. After 30 minutes' reaction, the reaction solution was analyzed, showing that it contained 8.9g of unreacted acetaldehyde, 17.9g of peracetic acid and 1.0g of AMP and that acetic acid was almost not produced.

EXAMPLE 20

The reaction system employed in Example 6 was charged with 24g of acetaldedhyde, 106g of acetone, 10g of acetone dissolving 0.03g of 2,4,6-trinitroresorcinol and 10g of methyl ethyl ketone dissolving 0.03g of cobalt naphthenate. Oxygen gas was then introduced into the flask at a rate of 300 to 400 ml per minute while vigorously stirring the solution at a rate of 900 r.p.m. and maintaining the reaction temperature at 20° C to 22° C. After one hour's reaction, the reaction solution was analyzed, showing that it contained 5.1g of unreacted acetaldehyde, 1.5g of acetic acid, 25.5g of peracetic acid and 3.9g of AMP.

EXAMPLE 21

The reaction system employed in Example 6 was charged with 24g of acetaldehyde, 56g of acetone, 10g of acetone dissolving 0.02g of 2,4,6-trinitrophenol, 10g of acetone dissolving 0.02g of 2,6-dinitrophenol, 10g of acetone dissolving 0.02g of pentachlorophenol, 20g of methyl ethyl ketone dissolving 0.02g of ferric naphthenate and 20g of methyl ethyl ketone dissolving 0.01g of manganese naphthenate. Oxygen gas was then introduced into the flask at a rate of 300 to 400 ml per minute while vigorously stirring the solution at a rate of 900 r.p.m. and maintaining the reaction temperature at 25° C to 30° C. After 30 minutes' reaction, the reaction solution was analyzed, showing that it contained 9.3g of unreacted acetaldehyde, 1.3g of acetic acid, 20.7g of peracetic acid and 2.3g of AMP.

EXAMPLE 22 k

The reaction system employed in Example 13 was charged with 44g of acetaldehyde, 350g of ethyl acetate, 0.02g of cobalt acetate, 0.01g of nickel acetate, 0.04g of 2,4,6-trinitroresorcinol and 0.03g of 2,4,6-trinitrophenol. Oxygen gas was then introduced into the flask at a rate of 300 to 400 ml per minute while vigorously stirring the solution at a rate of 900 r.p.m. and maintaining the reaction temperature 23° C to 25° C. After one hour's reaction, the reaction solution was analyzed, showing that it contained 14.0g of unreacted acetaldehyde, 1.8g of acetic acid, 41.8g of peracetic acid and 6.0g of AMP.

EXAMPLE 23

The reaction system employed in Example 13 was charged with 44g of acetaldehyde, 200g of methyl acetate, 100g of methyl ethyl ketone dissolving 0.1g of ferric naphthenate, 0.05g of pentachlorophenol and 0.03g of 2,4-dinitrophenol. Oxygen gas was then introduced into the flask under the pressure of 150 mm Hg (guage) at a rate of 300 to 400 ml per minute while vigorously stirring the solution at a rate of 900 r.p.m. and maintaining the reaction temperature at 18° C to 22° C. After 30 minutes' reaction, the reaction solution was analyzed, showing that it contained 18.0g of unreacted acetaldehyde, 3.0g of acetic acid, 25.8g of peracetic acid and 12.0g of AMP.

EXAMPLE 24

The reaction system employed in Example 4 was charged with 15g of acetaldehyde, 50g of methyl acetate, 50g of ethyl acetate, 0.001g of manganese acetate and 0.002g of 2,4,6-trinitrophenol. Oxygen gas was then introduced into the autoclave under the pressure of 2kg/cm$^2$ (gauge) while vigorously stirring the solution at a rate of 700 r.p.m. and maintaining the reaction temperature at 7° C to 12° C. After 40 minutes' reaction, the reaction solution was analyzed, showing that it contained 3.0g of unreacted acetaldehyde, 2.0g of acetic acid, 13.0g of peracetic acid and 4.1g of AMP.

EXAMPLE 25

The reaction system employed in Example 6 was charged with 24g of acetaldehyde, 116g of acetone, 10g of methyl ethyl ketone, 0.03g of cobalt naphthenate and 0.02g of high-grade nitric acid (60% aqueous solution). Oxygen gas was then introduced into the flask under the pressure of 150 mm Hg (gauge) at a rate of 300 to 400 ml per minute while vigorously stirring the solution at a rate of 900 r.p.m. and maintaining the reaction temperature at 20° C to 22° C. After 1 hour's reaction, the reaction solution was analyzed, showing that it contained 5.1g of unreacted acetaldehyde, 26.8g of peracetic acid and 4.2g of AMP and that acetic acid was almost not produced.

EXAMPLE 26

The reaction system employed in Example 13 was charged with 44g of acetaldehyde, 220g of acetone, 30g of methyl ethyl ketone, 0.02g of ferric nitrate (Fe(NO$_3$)$_3$.9H$_2$O), 0.01g of nickel naphthenate (nickel content: 10.5%), 0.01g of chromium naphthenate (chromium content: 9.8%), 0.01g of vanadium naphthenate (vanadium content: 9.5%) and 0.02g of high-grade nitric acid (60% aqueous solution). Oxygen gas was then introduced into the flask at a rate of 300 to 400 ml per minute while vigorously stirring the solution at a rate of 900 r.p.m. and maintaining the reaction temperature at 23° C to 25° C. After one hour's reaction, the reaction solution was analyzed, showing that it contained 6.1g of unreacted acetaldehyde, 48.7g of peracetic acid and 13.2g of AMP and that acetic acid was almost not produced.

EXAMPLE 27

The reaction system employed in Example 13 was charged with 44g of acetaldehyde, 300g of acetone, 30g of methyl ethyl ketone, 0.01g of ferric naphthenate, 0.01g of cobalt naphthenate and 0.03g of nitric acid (30% aqueous solution). Oxygen gas was then introduced into the flask at a rate of 300 to ;b 400 ml per minute while vigorously stirring the solution at a rate of 900 r.p.m. and maintaining the reaction temperature at 15° C to 18° C. After 20 minutes' reaction, the reaction solution was analyzed, showing that it contained 26.4g of unreacted acetaldehyde and 30.4g of peracetic acid and that acetic acid and AMP were almost not produced.

EXAMPLE 28

The reaction system employed in Example 4 was charged with 15g of acetaldehyde, 50g of methyl acetate, 80g of methyl ethyl ketone, 0.01g of ferric acetate, 0.01g of chromium naphthenate and 0.01g of high-grade nitric acid (60% aqueous solution). Oxygen gas was then introduced into the autoclave under the pressure of 2kg/cm$^2$ (gauge) while vigorously stirring the solution at a rate of 700 r.p.m. and maintaining the reaction temperature at 5° C to 10° C. After 30 minutes' reaction, the reaction solution was analyzed, showing that it contained 6.3g of unreacted acetaldehyde, 12.4g of peracetic acid and 2.0g of AMP and that acetic acid was almost not produced.

EXAMPLE 29

The reaction system employed in Example 6 was charged with 24g of acetaldehyde, 100g of acetone, 50g of ethyl acetate, 0.005g of acid cobalt pyromellitate and 0.01g of acid ferric maleate. Oxygen gas was then introduced into the flask at a rate of 300 to 400 ml per minute while vigorously stirring the solution at a rate of 900 r.p.m. and maintaining the reaction temperature at 20° C to 22° C. After one hour's reaction, the reaction solution was analyzed, showing that it contained 6.6g of unreacted acetaldehyde, 28.2g of peracetic acid and 1.4g of AMP and that acetic acid was almost not produced.

The acid cobalt pyromellitate used above was prepared as follows. To a 10% aqueous solution of pyromellitic acid heated at 90° C to 100° C was added a small amount (correspondng to about ½ mole of the pyromellitic acid used) of freshly prepared cobaltic hydroxide (blue-colored, gelatinous), and the cobaltic hydroxide was dissolved completely. The resulting brown solution was then concentrated to form a precipitate which was filtered, washed with warm water for several times and dried. The cobalt content in the resulting pyromellitate was 17.5%.

The acid iron maleate used above was prepared in the same manner as in the case of the acid cobaltic pyromellitate. In ths case, however, since the filterable precipitate was not formed from the concentrated solution, a small amount of acetone was added to the concentrated solution and the orange-colored precipitate thus formed was used after separating it from the mother jliquor and drying. The iron content in the resulting maleate was 17.9%.

EXAMPLE 30

The reaction system employed in Example 6 was charged with 44g of acetaldehyde, 220g of acetone and 0.02g of acid cobalt tartronate. Oxygen gas was then introduced into the flask at a rate of 300 to 400 ml per minute while vigorously stirring the solution at a rate of 900 r.p.m. and maintaining the reaction temperature at 23° C to 27° C. After one hour's reaction, the reaction solution was analyzed, showing that it contained 14.5g of unreacted acetaldehyde and 50.9g of peracetic acid and that acetic acid and AMP were almost not produced.

The acid cobalt tartronate used above was prepared in the same manner as in the case of the acid cobalt pyromellitate used in Example 29. The cobalt content in the resulting acid cobalt tartronate was 25.5%.

EXAMPLE 31

The reaction system employed in Example 6 was charged with 20g of acetaldehyde, 100g of acetone, 70g of methyl ethyl ketone, 0.01g of acid cobalt phthalate and 0.003g of acid manganese trimellitate. Oxygen gas was then introduced into the flask at a rate of 300 to 400 ml per minute while vigorously stirring the solution at a rate of 900 r.p.m. and maintaining the reaction temperature at 16° C to 19° C. After 40 minutes' reaction, the reaction solution was analyzed, showing that it contained 10.3g of unreacted acetaldehyde, 15.2g of peracetic acid and 1.2g of AMP and that acetic was almost not produced.

The acidic salts used above were prepared by adding the calculated amount of polycarboxylic acid sufficient to form a sodium salt of one carboxylic group of said polycarboxylic acid to an aqueous solution of sodium bicarbonate, heating the mixture for a while to prepare an aqueous solution of hydrogen sodium polycarboxylate, adding thereto a calculated amount of an aqueous solution of heavy metal nitrate to form a precipitate which was then thoroughly washed with hot water and dried. The resulting acid cobalt phthalate and acid manganese trimellitate contained 18.4% cobalt and 16.2% manganese, respectively.

EXAMPLE 32

The reaction system employed in Example 13 was charged with 44g of acetaldehyde, 300g of acetone and 0.003 of acid manganese pyromellitate. Oxygen gas was then introduced into the flask under the pressure of 150 mm Hg (gauge) at a rate of 300 to 400 ml per minute while vigorously stirring the solution at a rate of 900 r.p.m. and maintaining the reaction temperature at 20° C to 23° C. After 1.5 hours' reaction, the reaction solution was analyzed, showing that it contained 13.6g of unreacted acetaldehyde, 3.0g of acetic acid, 36.5g of peracetic acid and 9.6g of AMP.

The acid manganese pyromellitate used above was prepared in the same manner as described in Example 31. The resulting pyromellitate contained 15.7% managanese.

EXAMPLE 33

The reaction system employed in Example 13 was charged with 44g of acetaldehyde, 200g of acetone, 200g of methyl ethyl ketone and 0.06g of acid ferric hexahydrophthalate. Oxygen gas was then introduced into the flask at a rate of 300 to 400 ml per minute while vigorously stirring the solution at a rate of 900 r.p.m. and maintaining the reaction temperature of 16° C to 20° C. After 50 minutes' reaction, the reaction solution was analyzed, showing that it contained 14.0g of unreacted acetaldehyde, 39.5g of peracetic acid and 9.6g of AMP and that acetic acid was almost not produced.

The acid ferric hexahydro-phthalate used above was prepared in the same manner as described in Example 31. The resulting hexahydro-phthalate contained 12.0% iron.

EXAMPLE 34

The reaction system employed in Example 6 was charged with 20g of acetaldehyde, 150g of methyl ethyl ketone and 0.01g of acid ferric phthalate. Oxygen gas was then introduced into the flask under the pressure of 100 mm Hg (gauge) at a rate of 300 to 400 ml per minute while vigorously stirring the solution at a rate of 900 r.p.m. and maintaining the reaction temperature at 22° C to 26° C. After 30 minutes' reaction, the reaction solution was analyzed, showing that it contained 10.6g of unreacted acetaldehyde, 14.5g of peracetic acid and 1.3g of AMP and that acetic acid was almost not produced.

The acidic ferric phthalate used above was prepared in the same manner as described in Example 31. The resulting phthalate contained 13.7% iron.

EXAMPLE 35

The reaction system employed in Example 17 was charged with 20g of acetaldehyde, 70g of acetone, 70g of methyl acetate and 0.005g of acid ferric pyromellitate. Oxygen gas was then introduced into the autoclave under the pressure of 2 kg/cm$^2$ (gauge) while vigorously stirring the solution at a rate of 700 r.p.m. and maintaining the reaction temperature at 15° to 20° C. After one hour's reaction, the reaction solution was analyzed, showing that it contained 12.5g of unreacted acetaldehye and 12.8g of peracetic acid and that acetic acid and AMP were almost not produced.

The acid ferric pyromellitate used above contained 10.5% iron.

EXAMPLE 36

The reaction system employed in Example 17 was charged with 24g of acetaldehyde, 126g of acetone, 0.01g of acid cobalt fumarate and 0.01g of acid ferric tartronate. Oxygen gas was then introduced into the autoclave under the pressure of 2 kg/cm$^2$ (gauge) while vigorously stirring the solution at a rate of 700 r.p.m. and maintaining the reaction temperature at 10° C to 15° C. After 1 hour's reaction, the reaction solution was analyzed, showing that it contained 7.2g of unreacted acetaldehyde, 1.6g of acetic acid, 21.9g of peracetic acid and 4.0g of AMP.

The acid cobalt fumarate and acid ferric tartronate used above were prepared in the same manner as described in Example 29. The resulting acid cobalt fumarate and acid ferric tartronate contained 26.1% cobalt and 16.8% iron, respectively.

EXAMPLE 37

The reaction system employed in Example 6 was charged with 24g of acetaldehyde, 126g of acetone and 0.015g of 2,4,6-trinitroresorcin monophenolate. Oxygen gas was then introduced in the flask at a rate of 300 to 400 ml per minute while vigorously stirring the solution at a rate of 800 r.p.m. and maintaining the reaction temperature at 18° C to 22° C. During the reaction, the reaction solution was sampled occasionally and analyzed to determine peracetic acid and AMP production curves. From the results of the analysis, the oxygen absorption rate and the selectivity to peracetic acid and AMP were calculated as indicated in the table below.

| Metal component | Maximum amount of absorbed oxygen (mol % to acetaldehyde used) | Selectivity at 20%-conversion (%) (based on oxygen reacted) | | Selectivity at 60%-conversion (%) (based on oxygen reacted) | |
|---|---|---|---|---|---|
| | | Peracetic acid | AMP | Peracetic acid | AMP |
| Iron* | 59 | 66 | 34 | 42 | 10 |
| Iron | 74 | 100 | 0 | 91 | 9 |
| Cobalt* | 59 | 69 | 31 | 35 | 7 |
| Cobalt | 71 | 100 | 0 | 94 | 6 |
| Nickel* | 28 | 25 | 73 | — | — |
| Nickel | 23 | 87 | 13 | 48 | 11 |
| Copper* | 25 | 23 | 77 | — | — |
| Copper | 19 | 73 | 17 | 36 | 3 |
| Chromium* | 24 | 24 | 74 | — | — |
| Chromium | 23 | 82 | 18 | 57 | 8 |

(*Results of comparative experiments using naphthenates of indicated metals. The experiments using nickel, copper and chromium naphthenates as catalysts were discontinued before the reaction rate of oxygen reached 60%.)

The monophenolate used above was prepared by adding a calculated amount of heavy metal hydroxide or carbonate (gelatinous), which was freshly prepared from a nitrate and sodium bicarbonate, to a 10% aqueous solution of 2,4,6-trinitroresorcine heated to 60° C to 70° C, removing the insoluble material from the resulting solution, concentrating the solution to crystallize out the precipitate which was then filtered, washed with a small amount of cold water and dried.

EXAMPLE 38

The reaction system employed in Example 17 was charged with 15g of acetaldehyde, 70g of methyl ethyl ketone, 70g of ethyl acetate and 0.005g of 2,4,6-trinitroresoncinol monophenolate (metal component: iron). Oxygen gas was then introduced into the autoclave under the pressure of 2 kg/cm² (gauge) while vigorously stirring the solution at a rate of 700 r.p.m. and maintaining the reaction temperature at 15° C to 20° C. After one hour's reaction, the reaction solution was analyzed, showing that it contained 4.2g of unreacted acetaldehyde, 15.5g of acetic acid and 2.5g of AMP and that acetic acid was almost not produced.

EXAMPLE 39

The reaction system employed in Example 6 was charged with 44g of acetaldehyde, 120g of acetone, 0.02g of iron trichloroacetate and 0.01g of concentrated hydrochloric acid (commercially available, highgrade). Oxygen gas was then introduced into the flask at a rate of 300 to 400 ml per minute while vigorously stirring the solution at a rate of 800 r.p.m. and maintaining the reaction temperature at 20° C to 24° C. After 1.5 hours' reaction, the reaction solution was analyzed, showing that it contained 10.6g of unreacted acetaldehyde, 10.8g of acetic acid, 30.4g of peracetic acid and 10.8g of AMP.

When, in the above reaction, hydrochloric acid was not added, the resulting reaction solution contained 14.5g of unreacted acetaldehyde, 13.2g of acetic acid, 20.5g of peracetic acid and 10.8g of AMP.

The ferric trichloroacetate used above was prepared from a 50% aqueous solution of 1 mol of trichloroacetic acid and ⅓ mole of freshly prepared ferric hydroxide following the procedure illustrated in Example 29.

EXAMPLE 40

The reaction system employed in Example 6 was charged with 24g of acetaldehyde, 76g of acetone, 50g of methyl ethyl ketone, 0.015g of ferric picrate and 0.02g of 20% hydrochloric acid. Oxygen gas was then introduced into the flask at a rate of 300 to 400 ml per minute while vigorously stirring the solution at a rate of 800 r.p.m. and maintaining the reaction temperature at 22° C to 26° C. This reaction had an induction period of 2 hours and proceeded rapidly after the lapse of said induction period. After one hour from the lapse of the induction period, the reaction solution was analyzed, showing that it contained 8.4g of unreacted acetaldehyde, 20.7g of peracetic acid and 4.9g of AMP and that acetic acid was almost not produced.

When, in the above reaction, hydrochloric acid was not added, the reaction did not occur over 4 hours.

The ferric picrate used above was prepared as follows. To an aqueous solution of picric acid (prepared by dissolving 2.3g of picric acid in 100 cc of water), was added an equimolar amount of ferric hydroxide. The mixture was then heated well on the water bath. After most of the water in the mixture was vaporized off, the residue was dissolved in warm water to remove the insoluble material. The resulting aqueous solution was concentrated to form at first orange-yellow precipitate of ferric picrate which was then filtered and dried.

EXAMPLE 41

The reaction system employed in Example 17 was charged with 20g of acetaldehyde, 160g of ethyl acetate, 0.05g of cobalt picrate and 10g of acetone containing 0.01g of hydrogen chloride. Oxygen gas was then introduced into the flask under the pressure of 2 kg/cm² (gauge) while vigorously stirring the solution at a rate of 600 r.p.m. and maintaining the reaction temperature at 15° C to 20° C. After 1 hour from the lapse of the induction period, the reaction solution was analyzed, showing that it contained 3.5g of unreacted acetaldyde, 2.6g of acetic acid, 19.3g of peracetic acid and 3.5g of AMP.

The cobalt picrate used above was was prepared in the same manner as described in Example 40.

EXAMPLE 42

The reaction system employed in Example 17 was charged with 20g of acetaldehyde, 50g of acetone, 50g of methyl acetate, 0.01g of ferric salt of pentachlorophenol, 0.01g of cobalt salt of 2,4-dinitrophenol and 0.01g of high-grade concentrated hydrochloric acid. Oxygen gas was then introduced into the flask under the pressure of 2 kg/cm²(gauge) while vigorously stirring the solution at a rate of 600 r.p.m. and maintaining the reaction temperature at 12° C to 16° C. After 1 hour from the lapse of the induction period, the reaction solution was analyzed, showing that it contained 12.5g of unreacted acetaldehyde, 1.6g of acetic acid, 7.0g of peracetic acid and 3.0g of AMP.

The ferric salt of pentachlorophenol and cobalt salt of 2,4-dinitrophenol used above were prepared in the same manner as described in Example 31 in which the sodium phenolate and the metal nitrates were used as the starting materials.

EXAMPLE 43

The reaction system employed in Example 6 was charged with 24g of acetaldehyde, 126g of acetone, 0.01g of cobalt nitrate ($Co(NO_3)_2 \cdot 6H_2$), 0.01g of ferric nitrate ($Fe(NO_3)_3 \cdot 9H_2O$) and 0.05g of high-grade concentrated hydrochloric acid. Oxygen was then introduced into the flask at a rate of 300 to 400 ml per minute while vigorously stirring the solution at a rate of 800 r.p.m. and maintaining the reaction temperature at 18° to 22° C. After 70 minutes' reaction solution was analyzed, showing that it contained 5.1g of unreacted acetaldehyde, 1.5g of acetic acid, 25.3g of peracetic acid and 3.9g of AMP.

When, in the above reaction, hydrochloric acid was not added, the resulting reaction solution contained 6.2g of unreacted acetaldehyde, 2.6g of acetic acid, 18.3g of peracetic acid and 7.2g of AMP.

EXAMPLE 44

The reaction system employed in Example 6 was charged with 30g of acetaldehyde, 100g of ethyl acetate, 0.03g of cobalt acetate ($Co(NO_3)_2 \cdot 6H_2O$) and 0.05g of 20% hydrochloric acid. Oxygen gas was then introduced into the flask at a rate of 300 to 400 ml per minute while vigorously stirring the solution at a rate of 800 r.p.m. and maintaining the reaction temperature at 20° C to 23° C. After 30 minutes' reaction, the reaction solution was analyzed, showing that it contained 9.3g of unreacted acetaldehyde, 1.2g of acetic acid, 31.1g of peracetic acid and 2.4g of AMP.

When, in the above reaction, hydrochloric acid was not added, the resulting reaction solution contained 13.4g of unreacted acetaldehyde, 2.0g of acetic acid, 15.6g of peracetic acid and 8.2g of AMP.

EXAMPLE 45

The reaction system employed in Example 6 was charged with 20g of acetaldehyde, 100g of ethyl acetate, 70g of acetone dissolving 0.005g of manganese nitrate (Mn(NO$_3$)$_2$.6H$_2$O) and 0.003g of chromium nitrate (Cr(NO$_3$)$_2$.9H$_2$O) and 10g of acetone dissolving 0.002g of hydrogen chloride gas. Oxygen gas was then introduced into the flask under the pressure of 150 mm Hg (gauge) at a rate of 300 to 400 ml per minute while vigorously stirring the solution at a rate of 800 r.p.m. and maintaining the reaction temperature at 15° C to 18° C. After 40 minutes' reaction, the reaction solution was analyzed, showing that it contained 6.2g of unreacted acetaldehyde, 2.2g of acetic acid, 19.0g of peracetic acid and 1.6g of AMP.

What is claimed is:

1. A process for the production of peracetic acid which comprises the steps of adding, to an inert solvent selected from the group consisting of acetone, ethyl acetate, methyl ethyl ketone, methyl acetate and benzene, acetaldehyde and at least one catalyst selected from the group consisting of strongly acidic carboxylic acids having a pKa value of less than 4.6. strongly acidic phenls containing (i) 1-2 hydroxy groups and (ii) said phenol also containing (a) more than two nitro groups of (b) more than three strong electron withdrawal groups, and nitric acid, and introducing oxygen gas or oxygen-containing gas into the resulting mixture while stirring said mixture and maintaining it at a temperature range of −5° C to 50° C.

2. A process as set forth in claim 1, wherein the strongly acidic carboxylic acids are those having pKa of less than 4.6 selected from the group consisting of formic acid; aliphatic and aromatic polycarboxylic acids; aliphatic carboxylic acids having functional groups selected from the group consisting of a hydroxy group, a carbonyl group, an amino group, a halogen group, a nitro group, an aldehyde group and an ether linkage; and aromatic carboxylic acids having functional groups selected from the group consisting of a nitro group, a hydroxy group, a halogen group, an aldehyde group, an ether linkage and the like.

3. A process for the production of peracetic acid which comprises the steps of adding, to an inert solvent selected from the group consisting of acetone, ethyl acetate, methyl ethyl ketone, methyl acetate and benzene, acetaldehyde, at least one catalyst selected from the group consisting of strongly acidic carboxylic acids having pKa of less than 4.6, strongly acidic phenols containing (i) 1-2 hydroxy groups and (ii) said phenol also containing (a) more than two nitro groups or (b) more than three strong electron withdrawal groups, and nitric acid, plus at least one catalyst selected from the group consisting of the soluble salts of valence-changeable heavy metal selected from the group consisting of iron, cobalt, nickel, manganese, copper, vanadium and chromium, and introducing oxygen gas or oxygen-containing gas into the resulting mixture while stirring said mixture and maintaining it at a temperature range of −5° C to 50° C.

4. A process as set forth in claim 3 wherein said soluble salts of valence-changeable heavy metal are the metal salts of aliphatic acids, naphthenates, benzoates, acetyl acetenates and nitrates.

5. A process for the production of peracetic acid which comprises the steps of adding to an inert solvent selected from the group consisting of acetone, ethyl acetate, methyl ethyl ketone, methyl acetate and benzene, acetaldehyde and at least one catalyst selected from the group consisting of (i) acid salts of polycarboxyic acids having pKa of less than 4.6, containing a valence-changeable heavy metals as the metal component and being soluble in the reaction solution, and (ii) monophenolates of strongly acidic dihydric phenols containing (a) 1-2 hydroxy groups and (b) said phenols also containing more than two nitro groups, or more than three halogen or cyano groups, said monophenolates also containing a valence-changeable heavy-metal component selected from the group consisting of iron, cobalt, nickel, manganese, copper, vanadium and chromium, and being soluble in the reaction solution, and introducing oxygen gas or oxygen-containing gas into the resulting mixture while stirring said mixture and maintaining it at a temperature range of −5° C to 50° C.

6. A process for the production of peracetic acid which comprises the steps of adding, to an inert solvent selected from the group consisting of acetone, ethyl acetate, methyl ethyl ketone, methyl acetate and benzene, acetaldehyde and at least one catalyst selected from the group consisting of valance-changeable heavy-metal salts selected from the group consisting of iron, cobalt, nickel, manganese, copper, vanadium and chromium, containing strongly acidic monocarboxylic acids having a pKa value of less than 4.6, or nitric acid as the acid component, plus hydrogen chloride or its aqueous solution, and introducing oxygen gas or oxygen-containing gas into the resulting mixture while stirring said mixture and maintaining it at a temperature range of −5° C to 50° C.

* * * * *